United States Patent
Simanzhenkov et al.

(10) Patent No.: US 9,630,893 B2
(45) Date of Patent: *Apr. 25, 2017

(54) INHERENTLY SAFE ODH OPERATION

(71) Applicant: NOVA Chemicals (International) S.A., Fribourg (CH)

(72) Inventors: Vasily Simanzhenkov, Calgary (CA); Xiaoliang Gao, Calgary (CA); Edward Christopher Foy, Calgary (CA); Leonid Modestovich Kustov, Moscow (RU); Aleksey Victorovich Kucherov, Moscow (RU); Elena Dmitrievna Finashina, Moscow (RU)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/370,572

(22) Filed: Dec. 6, 2016

(65) Prior Publication Data

US 2017/0081261 A1  Mar. 23, 2017

Related U.S. Application Data

(63) Continuation of application No. 14/524,269, filed on Oct. 27, 2014.

(30) Foreign Application Priority Data

Nov. 21, 2013  (CA) .................................... 2833822

(51) Int. Cl.
  *C07C 5/48*   (2006.01)
  *B01J 27/057*  (2006.01)
  *B01J 35/10*  (2006.01)

(52) U.S. Cl.
  CPC ............. *C07C 5/48* (2013.01); *B01J 27/0576* (2013.01); *B01J 35/1019* (2013.01); *C07C 2527/057* (2013.01)

(58) Field of Classification Search
  CPC .. C07C 11/04; C07C 5/48; C07C 7/12; C07C 2521/06; C07C 2523/22; C07C 2523/28; C07C 2523/887; C07C 2527/057; B01J 2523/00; B01J 2523/55; B01J 2523/56; B01J 2523/64; B01J 2523/68; B01J 19/242; B01J 19/2475; B01J 2208/00628; B01J 2208/00637; B01J 2208/00716; B01J 2219/00263; B01J 27/0576; B01J 35/1014; B01J 8/009; B01J 8/041
  See application file for complete search history.

(56) References Cited

U.S. PATENT DOCUMENTS

| | | | |
|---|---|---|---|
| 3,420,911 A | 1/1969 | Woskow et al. |
| 3,420,912 A | 1/1969 | Woskow et al. |
| 3,904,703 A | 9/1975 | Lo et al. |
| 4,250,346 A | 2/1981 | Young et al. |
| 4,450,313 A | 5/1984 | Eastman et al. |
| 4,524,236 A | 6/1985 | McCain |
| 4,596,787 A | 6/1986 | Manyik et al. |
| 4,899,003 A | 2/1990 | Manyik et al. |
| 5,202,517 A | 4/1993 | Minet et al. |
| 6,521,808 B1 | 2/2003 | Ozkan et al. |
| 6,566,573 B1 | 5/2003 | Bharadwaj et al. |
| 6,624,116 B1 | 9/2003 | Bharadwaj et al. |
| 6,818,189 B1 | 11/2004 | Adris et al. |
| 6,891,075 B2 | 5/2005 | Liu |
| 7,319,179 B2 | 1/2008 | Lopez Nieto et al. |
| 7,998,438 B2 | 8/2011 | Weiss |
| 8,394,345 B2 | 3/2013 | Dieterle et al. |
| 2010/0256432 A1 | 10/2010 | Arnold et al. |

FOREIGN PATENT DOCUMENTS

| | | |
|---|---|---|
| GB | 12 13 181 | 11/1970 |
| JP | 1995053414 A | 2/1995 |
| WO | 2005/058498 A1 | 6/2005 |
| WO | 2006/130288 A1 | 12/2006 |

OTHER PUBLICATIONS

Peri, J.B. and Hensley, Jr., A.L.; The Surface Structure of Silica Gel; The Journal of Physical Chemistry, vol. 72, No. 8, Aug. 1968, pp. 2926-2933.

*Primary Examiner* — Sharon Pregler
(74) *Attorney, Agent, or Firm* — Julie L. Heinrich

(57) ABSTRACT

In the operation of an oxidative dehydrogenation (ODH) process, it is desirable to remove oxygen in the product stream for a number of reasons, including to reduce oxidation of the product. This may be achieved by having several pre-reactors upstream of the main reactor having a catalyst system containing labile oxygen. The feed passes through one or more reactors saturated with labile oxygen. When the labile oxygen is consumed through a valve system, the pre-reactor accepts product from the main reactor and complexes reactive oxygen in the product stream until the catalyst system is saturated with labile oxygen. Then the reactor becomes a pre-reactor and another pre-reactor becomes a scavenger.

11 Claims, 12 Drawing Sheets

INHERENTLY SAFE ODH OPERATION

CROSS REFERENCE TO RELATED PATENT APPLICATION

This application is a continuation of U.S. application Ser. No. 14/524,269, filed on Oct. 27, 2014, entitled "Inherently Safe ODH Operation", which is herein incorporated by reference in its entirety.

FIELD

The present disclosure relates to an oxidative dehydrogenation reactor and process having improved safety. Typically, the process of oxidative dehydrogenation of alkanes to alkenes involves passing a stream of one or more alkanes over an oxidative dehydrogenation catalyst at temperatures from about 300° C. to about 750° C. in the presence of oxygen or an oxygen containing gas. Great care needs to be taken to prevent the reactor feed mixture from reaching an explosive limit. Additionally, in some examples, it is desirable to remove residual oxygen from the product stream as this could lead to a process fire.

BACKGROUND

The use of various ferrites in a steam cracker to produce olefins from paraffins is known. Introducing ferrites such as zinc, cadmium, and manganese ferrites (i.e., mixed oxides with iron oxide) into a dehydrogenation zone at a temperature from about 250° C. up to about 750° C. at pressures less than 100 psi (689.476 kPa) for a time less than 2 seconds, typically from 0.005 to 0.9 seconds are also known. These reactions appear to take place in the presence of steam that may tend to shift the equilibrium in the "wrong" direction. Additionally, the reaction does not take place in the presence of a catalyst.

In addition, it is known that nickel ferrite may be used in the oxidative dehydrogenation process using reaction conditions comparable to those noted above.

In some Petro-Tex patents, the metal ferrite (e.g., M $FeO_4$ where, for example, M is Mg, Mn, Co, Ni, Zn or Cd) is circulated through the dehydrogenation zone and then to a regeneration zone where the ferrite is re-oxidized and then fed back to the dehydrogenation zone.

It is interesting to note that the ferrite reversible takes up and releases oxygen.

Also known is a catalyst for the oxidative dehydrogenation of a paraffin (alkane) such as ethane. The gaseous feedstock comprises at least the alkane and oxygen, but may also include diluents (such as, argon, nitrogen, etc.) or other components (such as, water or carbon dioxide). The dehydrogenation catalyst comprises at least about 2 weight % of NiO and a broad range of other elements preferably Nb, Ta, and Co. While NiO is present in the catalyst, it does not appear to be the source of the oxygen for the oxidative dehydrogenation of the alkane (ethane).

Also known are sol gel supported catalysts for the oxidative dehydrogenation of ethane to ethylene. The catalyst appears to be a mixed metal system, such as, Ni—Co—Mo, V—Nb—Mo possibly doped with small amounts of Li, Na, K, Rb, and Cs on a mixed silica oxide/titanium oxide support. Again, the catalyst does not provide the oxygen for the oxidative dehydrogenation, rather gaseous oxygen is included in the feed.

Also known is a catalyst of the composition $LiO$—$TiO_2$, which is characterized by a low ethane conversion not exceeding 10%, in spite of a rather high selectivity to ethylene (92%). The catalyst is used in a high temperature process of oxidative dehydrogenation, which is close to or higher than 650° C.

The preparation of a supported catalyst usable for low temperature oxy-dehydrogenation of ethane to ethylene has been disclosed. A supported catalyst for the low temperature gas phase oxydehydrogenation of ethane to ethylene is prepared by (a) preparing a precursor solution having soluble and insoluble portions of metal compounds; (b) separating the soluble portion; (c) impregnating a catalyst support with the soluble portion and (d) activating the impregnated support to obtain the catalyst. The calcined catalyst has the composition $Mo_aV_bNb_cSb_dX_e$. X is nothing or Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, Mn and/or W; a is 0.5 to 0.9, b is 0.1 to 0.4, c is 0.001 to 0.2, d is 0.001 to 0.1, e is 0.001 to 0.1 when X is present.

Another example of the low temperature oxy-dehydrogenation of ethane to ethylene using a calcined oxide catalyst containing molybdenum, vanadium, niobium and antimony is the calcined catalyst containing $Mo_aV_bNb_cSb_dX_e$ in the form of oxides. The catalyst is prepared from a solution of soluble compounds and/or complexes and/or compounds of each of the metals. The dried catalyst is calcined by heating at 220 to 550° C. in air or oxygen. The catalyst precursor solutions may be supported on to a support, e.g., silica, aluminum oxide, silicon carbide, zirconia, titania or mixtures of these. The selectivity to ethylene may be greater than 65% for a 50% conversion of ethane.

Also disclosed elsewhere are Pt—Sn—Sb—Cu—Ag monolith systems that have been tested in an auto-thermal regime at T>750° C., the starting gas mixture contained hydrogen ($H_2$:$O_2$=2:1, GHSV=80,000 $h^{-1}$). The catalyst composition is different from that of the present disclosure and does not contemplate the use of molecular hydrogen in the feed.

Also disclosed elsewhere are mixed metal oxide catalysts of V—Mo—Nb—Sb. At 375 to 400° C., the ethane conversion reached 70% with the selectivity close to 71 to 73%. However, these parameters were achieved only at very low gas hourly space velocities less than 900 $h^{-1}$ (i.e., 720 $h^{-1}$).

Japanese Patent 07053414 teaches a silica supported catalyst of the formula $Mo_1.V_{0.3}Nb_{0.12}Te_{0.23}O_n$ where n satisfies the valence of the catalyst for the dehydrogenation of ethane.

Also disclosed elsewhere are Mo—V—Te—Nb—O oxide catalysts that provide an ethane conversion of 50 to 70% and selectivity to ethylene up to 95% (at 38% conversion) at 360 to 400° C. The catalysts have the empirical formula $MoTe_hV_iNb_jA_kO_x$, where A is a fifth modifying element. The catalyst is a calcined mixed oxide (at least of Mo, Te, V and Nb), optionally supported on: (i) silica, alumina and/or titania, preferably silica at 20 to 70 wt % of the total supported catalyst or (ii) silicon carbide. The supported catalyst is prepared by conventional methods of precipitation from solutions, drying the precipitate then calcining.

A known preparation of a Mo—Te—V—Nb composition involves preparing a slurry by combining an inert ceramic carrier with at least one solution comprising ionic species of Mo, V, Te, and Nb, drying the slurry to obtain a particulate product, pre-calcining the dried product at 150 to 350° C. in an oxygen containing atmosphere and calcining the dried product at 350 to 750° C. under inert atmosphere. The catalyst prepared exhibits the activity and selectivity in the oxidation reaction comparable to the non-supported catalyst.

A process for preparation of ethylene from gaseous feed comprising ethane and oxygen involving contacting the feed with a mixed oxide catalyst containing vanadium, molybdenum, tantalum and tellurium in a reactor to form effluent of ethylene has been disclosed. The catalyst has a selectivity for ethylene of 50 to 80%, thereby allowing oxidation of ethane to produce ethylene and acetic acid with high selectivity. The catalyst has the formula $Mo_1N_{0.3}Ta_{0.1}Te_{0.3}O_z$. The catalyst is optionally supported on a support selected from porous silicon dioxide, ignited silicon dioxide, kieselguhr, silica gel, porous and nonporous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, aluminum silicate, silicon nitride, silicon carbide, and glass, carbon, carbon-fiber, activated carbon, metal-oxide or metal networks and corresponding monoliths; or is encapsulated in a material (preferably silicon dioxide ($SiO_2$), phosphorus pentoxide ($P_2O_5$), magnesium oxide (MgO), chromium trioxide ($Cr_2O_3$), titanium oxide ($TiO_2$), zirconium oxide ($ZrO_2$) or alumina ($Al_2O_3$). However, the methods of preparation of the supported compositions involve the procedures of wet chemistry (solutions are impregnated into the solid support and then the materials are dried and calcined).

A ceramic tube for use in the conventional dehydrogenation of ethane to ethylene. The "tube" is a ceramic membrane. The ethane flows inside the tube and hydrogen diffuses out of the tube to improve the reaction kinetics. The reactive ceramic is 5 microns thick on a 1.5 to 2 mm thick support.

SABIC teaches a process in which ceramic pellets are packed around a tubular reactor and different reactants flow around the outside and inside of the tube for use in the oxidative dehydrogenation of ethane to ethylene.

A zoned or layered oxidative reactor in which following a zone for oxidative dehydrogenation there is an "oxidation zone" following a dehydrogenation zone to oxidize the hydrogen to water is known. Following the oxidation zone, there is an adsorption bed to remove water from the reactants before they enter a subsequent dehydrogenation zone. This is to reduce the impact of water on downstream dehydrogenation catalysts.

Methods to remove residual oxygen from the product stream have been disclosed. A combustible, such as hydrogen or a hydrocarbon, may be added to the product stream to eliminate residual oxygen. The disclosure refers to a catalyst but does not disclose its composition. As noted above, it may then be necessary to treat the product stream to eliminate water.

Also known are processes for the partial catalytic oxidation of a hydrocarbon to a final product, such as, propene to acrolein or acrylic acid. The process appears to operate outside the explosive limits of propylene (Col. 32-33). Additionally, the final product stream contains small amounts of oxygen (1.5 to 3.5 vol. %, Col. 37, line 10). The residual oxygen content in the final product (acrylic acid) does not appear to be a concern for the inventors. In these processes, the catalyst is not regenerated in situ, it is replaced with new catalyst.

Other disclosures teach a coupling process for lower hydrocarbons to produce higher hydrocarbons involving halogenation (bromination) followed by an oxidative removal of halogen and coupling of the intermediate compounds to produce the final product. This is of interest as it teaches a forward, reverse feed to burn coke off one of the catalysts used in the process. This disclosure teaches away for recycling product through a reaction zone to eliminate residual oxygen.

It has been known to remove residual oxygen from the product stream of an oxidative dehydrogenation process by consuming the oxygen by burning hydrocarbons or hydrogen. This is expensive and reduces yields of and selectivity for the desired hydrocarbon.

Disclosed herein are simple ways to reduce the oxygen content in the product stream from an oxidative dehydrogenation reaction by passing the stream over a catalyst bed, to extract oxygen from the product stream and at least partially provide a source of oxygen for the catalyst.

SUMMARY

In one embodiment, a process is provided for the catalytic oxidative dehydrogenation of one or more $C_{2-4}$ alkanes comprising n pre-reactors for the oxidative dehydrogenation of said alkanes in the presence of a mixed metal oxide oxidative dehydrogenation catalyst system which takes up-oxygen in the catalyst, where n is an integer of 2 or more, and one or more downstream main oxidative reactors comprising: a. passing a feed stream comprising said one or more $C_{2-4}$ alkanes through one or more of n−1 of the pre-reactors at a temperature from about 300° C. to about 500° C. and a pressure from about 3.447 kPag to about 689.47 kPag (about 0.5 to about 100 psig) to oxidatively dehydrogenate at least a portion of the feedstream until the oxidative dehydrogenation catalyst is depleted of reactive oxygen;

ii) diverting the feed stream from the pre-reactor(s) in which the oxidative dehydrogenation catalyst is depleted of reactive oxygen to a pre-reactor in which the oxidative dehydrogenation catalyst is substantially saturated with reactive oxygen;

iii) passing the product stream from said n−1 pre-reactor(s) together with additional oxygen feed to one or more downstream reactors at a temperature from about 300° C. to about 500° C. and a pressure from about 3.447 kPag to about 689.47 kPag (about 0.5 to about 100 psig) for the oxidative dehydrogenation of said one or more $C_{2-4}$ alkanes;

iv) removing a product stream from said one or more downstream reactors comprising corresponding $C_{2-4}$ alkenes, unreacted $C_{2-4}$ alkanes, unreacted oxygen and water vapor and passing it through one or more pre-reactors depleted of reactive oxygen at a temperature from about 50° C. to about 300° C. and a pressure from about 3.447 kPag to about 689.46 kPag to complex the oxygen in the product stream and increase the reactive oxygen saturation of the oxidative dehydrogenation catalyst and recovering a product stream substantially free of oxygen;

v) continuing step iv) until either:
a) there is another pre-reactor more depleted of reactive oxygen than that through which the product stream is being passed; or
b) the oxidative dehydrogenation catalyst in pre-reactor is substantially complexed with reactive oxygen;

vi) switching the flow of product stream from the formerly reactive oxygen depleted pre-reactor to a more reactive oxygen depleted pre-reactor; and vii) optionally completely saturating the oxidative dehydrogenation catalyst in the formerly reactive oxygen depleted pre-reactor with reactive oxygen; and viii) bringing on line the formerly oxygen depleted pre-reactor.

In a further embodiment the oxidative dehydrogenation catalyst in any rector is independently selected from:
i) catalysts of the formula

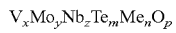

wherein Me is a metal selected from Ta, Ti, W, Hf, Zr, Sb and mixtures thereof; and x is from about 0.1 to about 3 provided that when Me is absent x is greater than 0.5;

y is from about 0.5 to about 1.5;

z is from about 0.001 to about 3;

m is from about 0.001 to about 5;

n is from 0 to about 2; and p is a number to satisfy the valence state of the mixed oxide catalyst ii) catalysts of the formula

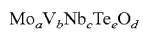

wherein:

a is from about 0.75 to about 1.25, or, for example, from about 0.90 to about 1.10;

b is from about 0.1 to about 0.5, or, for example, from about 0.25 to about 0.3;

c is from about 0.1 to about 0.5, or, for example, from about 0.1 to about 0.3;

e is from about 0.1 to about 0.3 or, for example, from about 0.1 to about 0.2; and d is determined by the oxidation states of the other elements.

In a further embodiment, said one or more downstream reactors are operated at a gas hourly space velocity (GHSV) may be from about 500 to about 30000 h$^{-1}$, or, for example, greater than 1000 h$^{-1}$.

In a further embodiment, the pre-reactors are fixed bed reactors and the oxidative dehydrogenation catalyst is supported on an inert metal oxide support.

In a further embodiment, said one or more downstream reactors are selected from fixed bed reactors, fluidized or ebullient bed reactors and ceramic membrane reactors.

In a further embodiment, the process has a selectivity for said one or more $C_{2-4}$ alkenes of greater than about 85%, or, for example, greater than about 95%.

In a further embodiment, said one or more $C_{2-4}$ alkanes is ethane.

DETAILED DESCRIPTION

Numbers Ranges

Figure 1:
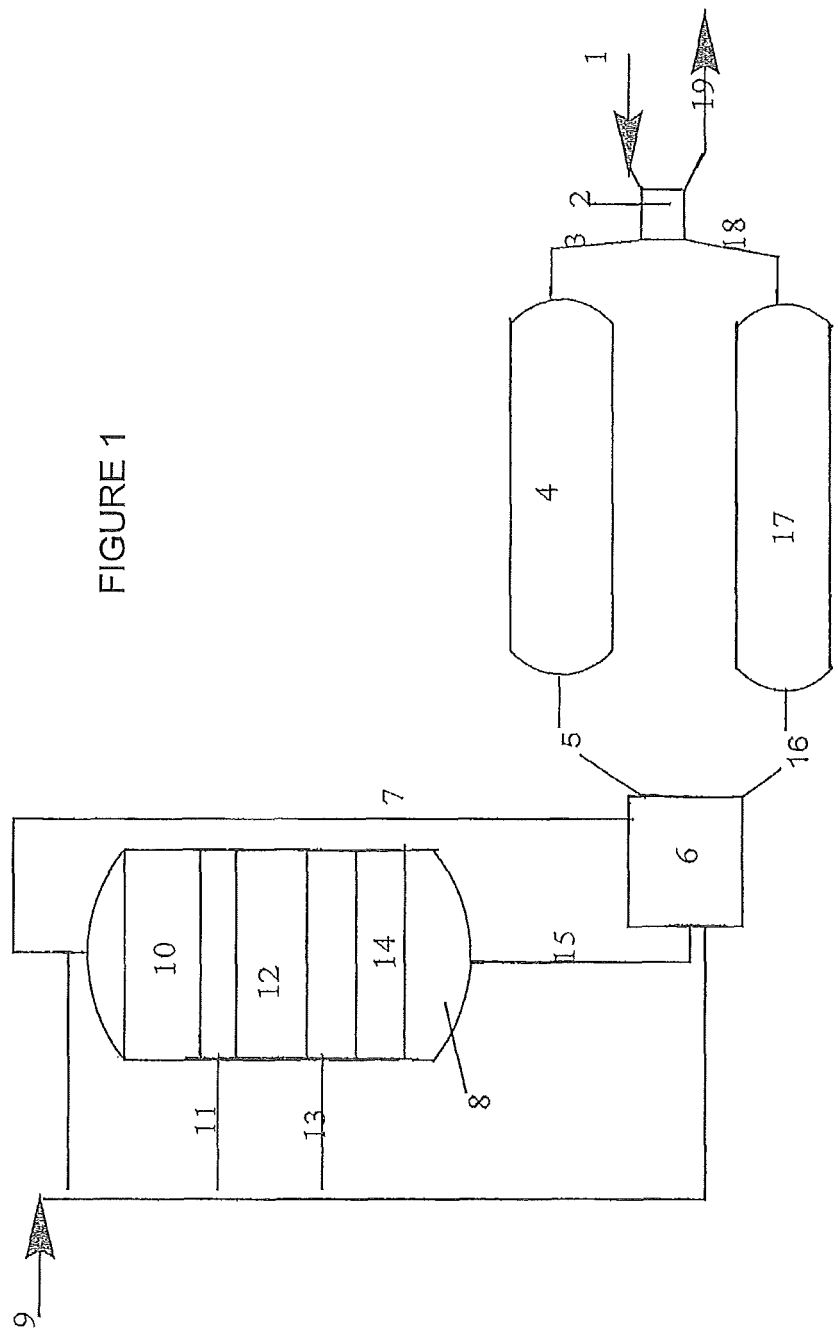
FIG. 1 is a schematic diagram of an apparatus and process flow to carry out the various embodiments described herein.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties desired. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, that the amounts of the components actually used will conform to the maximum of 100 percent.

In the disclosure, "reactive oxygen" means oxygen taken up by the oxidative dehydrogenation catalyst which is available to be used in the oxidative dehydrogenation reaction and removed from the catalyst.

In the disclosure, the term "reactive oxygen depleted", when referring to the catalyst in the pre-reactor, is not intended to mean absolute oxygen depletion. Rather, it means that the levels of residual reactive oxygen in the catalyst is sufficiently low so that there is less than 25%, or, for example, less than 15% or, for example, less than 10% of the maximum amount of oxygen which has been taken up by the catalyst. After giving up reactive oxygen, the catalysts comprise metal oxides which do not give up oxygen.

Substantially saturated with reactive oxygen means that not less than 60%, or, for example, more than 70%, or, for example, more than 85% of the reactive oxygen has been complexed with the oxidative dehydrogenation catalyst.

The Catalyst System

There are a number of catalysts which may be used in accordance with the various embodiments disclosed herein. The following catalyst systems may be used individually or in combination. One of ordinary skill in the art would understand that combinations should be tested at a laboratory scale to determine if there are any antagonistic effects when catalyst combinations are used.

In some embodiments, the family of catalysts comprise one or more catalysts selected from a mixed oxide catalyst of the formula i) $V_xMo_yNb_zTe_mMe_nO_p$, wherein Me is a metal selected from Ti, Ta, Sb, Hf, W, Y, Zn, Zr, La, Ce, Pr, Nd, Sm, Sn, Bi, Pb Cr, Mn, Fe, Co, Cu, Ru, Rh, Pd, Pt, Ag, Cd, Os, Ir, Au, and mixtures thereof; and x is from about 0.1 to about 3, or, for example, from about 0.5 to about 2.0 or, for example, from about 0.75 to about 1.5 provided that when Me is present x is greater than 0.5;

y is from about 0.5 to about 1.5, or, for example, from about 0.75 to about 1.0;

z is from about 0.001 to about 3, or, for example, from about 0.1 to about 2, or, for example, from about 0.5 to about 1.5;

m is from about 0.001 to about 5, or, for example, from about 1 to about 4;

n is from 0 to about 2, or, for example, n is 0, however, when Me is present n is, for example, from about 0.5 to about 1.5; and p is a number to satisfy the valence state of the mixed oxide catalyst; and ii) catalysts of the formula $Mo_aV_bNb_cTe_eO_d$ wherein a is from about 0.75 to about 1.25, or, for example, from about 0.90 to about 1.10;

b is from about 0.1 to about 0.5, or, for example, from about 0.25 to about 0.3;

c is from about 0.1 to about 0.5, or, for example, from about 0.1 to about 0.3;

e is from about 0.1 to about 0.3, or, for example, from about 0.1 to about 0.2; and d is determined by the oxidation states of the other elements.

In a further embodiment, in catalysts of group i) the ratio of x:m is from about 0.3 to about 10, or, for example, from about 0.5 to about 8, desirably from about 0.5 to about 6.

Generally, a solution is prepared of compounds of the metals selected for the catalyst, and either a particulate catalyst is formed or a supported catalyst is formed.

The methods of preparing the catalysts are known to those skilled in the art. For example, the catalyst may be prepared by mixing aqueous solutions of soluble metal compounds such as hydroxides, sulphates, nitrates, halides, lower ($C_{1-5}$) mono- or di-carboxylic acids and ammonium salts or the metal acid per se. For instance, the catalyst could be prepared by blending solutions such as ammonium metavanadate, niobium oxalate, ammonium molybdate, telluric acid, etc. The resulting solution is then dried, typically, in air at about 100 to about 150° C. and calcined in a flow of inert gas such as those selected from $N_2$, He, Ar, Ne and mixtures thereof at about 200 to about 600° C., or, for example, at about 300 to about 500° C. The calcining step may take from about 1 to about 20, or, for example, from about 5 to about 15, or, for example, about 10 hours. The resulting oxide is a friable solid typically insoluble in water.

The Support

There are several ways the oxidative dehydrogenation catalyst may be supported.

In one embodiment, the support may have a low surface area, for example, less than about 20 m$^2$/g, or, for example, less than about 15 m$^2$/g, or, for example, less than about 3.0 m$^2$/g for the oxidative dehydrogenation catalyst in the main reactor. For the oxygen scavenging catalyst a higher surface area is, for example, greater than about 100 m$^2$/g. The support may be prepared by compression molding. At higher pressures, the interstices within the ceramic precursor being compressed collapse. Depending on the pressure exerted on the support precursor, the surface area of the support may be from about 15 to about 0.5 m$^2$/g, or, for example, about 10 to about 0.5 m$^2$/g or, for example, from about 5 to about 0.5 m$^2$/g or, for example, from about 3.0 to about 0.5 m$^2$/g.

There is a safety advantage using low surface area supports in that there is a reduced probability that an interstitial space may be filled only with oxidant providing a source of ignition.

The low surface area support could be of any conventional shape, such as, spheres, rings, saddles, etc. These types of supports would be used in more conventional reactors where a mixed stream of gaseous reactants pass over the supported catalyst and the ethane is converted to ethylene. In an embodiment, the catalyst in the pre reactor are at least partially regenerated by passing the product stream from the main oxidative dehydrogenation reactor over them and abstracting residual oxygen from the product stream. Optionally, the pre-reactor could be isolated and further treated with oxygen or an oxygen containing gas.

In an alternate embodiment described below, the catalyst in the one or more downstream reactors (main reactors) may be supported on a surface of a permeable ceramic membrane defining at least part of the flow path for one reactant and the other reactant flows over the opposite surface of the ceramic to permit the oxidant and ethane to react on the ceramic surface.

In some embodiments, it is important that the support be dried prior to use. Generally, the support may be heated at a temperature of at least 200° C. for up to about 24 hours, typically, at a temperature from about 500° C. to about 800° C. for about 2 to about 20 hours, or, for example, about 4 to about 10 hours. The resulting support may be free of adsorbed water and may have a surface hydroxyl content from about 0.1 to about 5 mmol/g of support, or, for example, from about 0.5 to about 3 mmol/g of support.

The amount of the hydroxyl groups in silica may be determined according to the method disclosed by J. B. Peri and A. L. Hensley, Jr., in *J. Phys. Chem.*, 72 (8), 2926, 1968.

The dried support may then be compressed into shape by compression molding. Depending on the particle size of the support, it may be combined with an inert binder to hold the shape of the compressed part.

The support for the catalyst may be a ceramic or ceramic precursor formed from oxides, dioxides, nitrides, carbides and phosphates selected from silicon dioxide, fused silicon dioxide, aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, yttrium oxide, aluminum silicate, silicon nitride, silicon carbide and mixtures thereof. In one embodiment, the support could include a binder to help shape it.

Some examples of components for forming ceramic membranes include oxides of titanium, zirconium, aluminum, magnesium, silicon and mixtures thereof.

As noted above, the support in the main reactor should have a low surface area, for example, less than about 10 $m^2/g$, or, for example, less than about 5 $m^2/g$, or, for example, less than about 3 $m^2/g$. The support may be prepared by compression molding. At higher pressures, the interstices within the ceramic precursor being compressed collapse. Depending on the pressure exerted on the support precursor, the surface area of the support may be less than about 15 $m^2/g$. The support may be porous and may have a pore volume from about 0.1 to about 3.0 ml/g, or, for example, from about 0.3 to about 1.0 ml/g. The pore size of the ceramic may be small. Example pore sizes (diameter) range from about 3 to about 10 nm. The small pore diameter is helpful in the ceramic membrane application as it helps maintain the pressure drop across the membrane so that a break in the membrane is readily detected by a sudden change in pressure. Additionally, the small pore diameter promotes a more uniform distribution of the reaction over the entire catalyzed surface of the membrane. That is, if larger pores are used, a majority of the oxygen tends to diffuse through the portion of the ceramic the oxygen containing gas initially comes in contact with. The remaining portion of the ceramic is largely unused.

The ceramic support may be prepared from the ceramic material using conventional techniques: For example, the starting material may be cleaned, washed and dried (or spray dried) or produced from a sol/gel of the ceramic and optionally ground or milled to the appropriate particle size. The powder may be subjected to benefication, such as, acid or base washing to alter the pore size of the ceramic.

The resulting powder is dried or calcined to remove associated water as noted above (water of hydration, etc.) and may be formed into a suitable substrate, for example, tubular, by, for example, compression molding or isostatic compaction at pressures from about 5 to about 200 MPa (about 725 to about 29,000 psi), with or without a binder and sintering at temperatures to fuse the particles (e.g., at temperatures from about 0.5 to about 0.75 of the melting temperature of the ceramic material).

Other techniques may be used, such as, tape casting or slip casting of slurries and the subsequent "punching of" the shape, such as, circular, square or annular, etc. For example, annular sections could be "stacked" to produce a "tube".

While a tube is generally considered cylindrical, it could have any cross section shapes, such as, square, rectangular, hexagonal or stars, etc. In the case of a non-cylindrical tube, wall sections could be made by slip casting and then hermetically joining the wall sections together to form a central passage defined by an outer ceramic wall. The joints may be hermetically sealed to prevent oxygen coming in contact with the ethane feed and forming an explosive mixture. Glass cement or a ceramic cement or slip would be used for this purpose. A hermetic seal may also be at the ends of the tube where it enters and exits the reactor or joins to the steel parts of the reactor.

In some embodiments, once the ceramic tube is prepared, the catalyst may be deposited on the surface of the tube which may be in contact with the ethane.

The ceramic membrane may have a thickness from about 0.1 to about 10 cm, or, for example, from about 1 to about 8 cm, or, for example, from about 2 to about 7 cm.

While ceramics are strong they can be brittle. In some embodiments, the supporting structure has at least on one side, or, for example, the outside of the ceramic tube. In some embodiments, there is a support structure on the outside and inside of the tube. The structure may be in the form of a mesh or a web having holes there through to permit the oxygen containing gas to pass through the support and the ceramic to react at the surface of the tube bearing the catalyst. The support may be any material suitable for use at the reactor operating temperatures. From a cost point of view, a steel mesh is likely most cost effective. In some embodiments, the steel is a stainless steel. The support structure should provide sufficient integrity to the tube to permit a shutdown of the reactor, if the ceramic is breached (e.g., becomes cracked, etc.).

One or more tubes are then placed inside the reactor. In one embodiment, the reactor is designed to have a plug flow of feedstock (e.g., primarily, ethane) through a passage between the reactor shell and the ceramic tube and a flow of oxygen containing gas through the ceramic tube. There are a number of arrangements that come to mind. The reactor could comprise several shorter tubes placed end to end to provide a tube of appropriate length. Or the design could be similar to a core shell heat exchanger with a number of parallel tubes through which the oxygen containing gas is passed with and an enclosed shell providing a passage between the external wall of the reactor and the ceramic tubes defining a flow path for the ethane. The flow paths might be reversed (ethane on the interior and oxygen on the exterior of the tube).

In one embodiment of the invention, the catalyst in the main reactor is on a ceramic membrane and in the case of the pre-reactor, on a high surface particulate support as described below.

An embodiment of the invention in which the catalyst in the main reactor is in the form of granular beds having a low surface area are described in association with FIG. 1. Alkane feedstock, for example, ethane, flows through a line 1 to a valve set 2 and through line 3 to pre-reactor 4, one of a pair of pre-reactors 4 and 17. In pre-reactors 4 and 17 there is a single fixed bed of catalyst, not shown. The bed is held in place between two porous membranes or open metallic meshes of a small enough mesh size so that the particles will not pass out of the bed, again not shown. The feed passes through pre-reactor 4 and is partially oxidatively dehydrogenated and the catalyst bed is depleted of reactive oxygen. The partially dehydrogenated feed passes through exit line 5 from the pre-reactor 4 to another valve set 6. The partially dehydrogenated feed flows from valve set 6 via line 7 to the top of the downstream reactor 8. The oxidant, typically, air or oxygen or a mixture of oxygen and an inert gas such as nitrogen or argon flows through a line 9 and enters the feed line 7 near the top of reactor 8. The mixed feed of oxygen and partially dehydrogenated feed flow through three fixed beds of catalyst 10, 12 and 14. There is a space between the catalyst beds and additional oxygen is fed via lines 11 and 13 into the space between the catalyst beds. The substantially dehydrogenated product stream containing small amounts of oxygen (for example, less than about 5 vol. %, or, for example, less than about 3 vol %) is fed via line 15 to vale set 6. The dehydrogenated feed passes through valve set 6 via line 16 to pre-reactor 17 which is depleted or substantially depleted of reactive oxygen. As the product stream passes through pre-reactor 17, oxygen is extracted from it and the oxidative dehydrogenation catalyst becomes more saturated with reactive oxygen. The product stream substantially depleted of oxygen is fed via line 18 to valve set 2. The product passes from valve set 2 to line 19 for recovery and further processing.

When pre-reactor 4 is depleted of reactive oxygen then valve sets 2 and 6 are switched so that alkane feed is fed to pre-reactor 17 and product from reactor 8 is fed to pre-reactor 4 so that it becomes more saturated (charged) with reactive oxygen.

In some instances (e.g., on startup) oxygen may be fed to the pre-reactor containing the catalyst supported on a support having a high surface area typically greater than about 100 m$^2$/g, or, for example, greater than about 150 m$^2$/g a to "charge" it with oxygen. This is more to balance the reaction times between various pre-reactors so that a pre-reactor dehydrogenating feed stock will have a sufficiently long operation to permit full "charging" of a pre-reactor depleted of reactive oxygen.

It is important to minimize the potential for oxidizing product stream from line 15 and producing one or more of carbon monoxide and carbon dioxide. Such an oxidation consumes valuable feed and product stocks, introduces undesirable by-products and reduces the conversion and selectivity of the process. To minimize the undesirable further oxidation of the feed and product it is important that temperatures in the pre-reactor when adsorbing oxygen from the product, stream (e.g., chemisorption) is kept below the temperature for oxidative dehydrogenation (e.g., from about 50° C. to about 300° C., or, for example, less about 270° C.). In the pre-reactor during the chemisorption or oxygen scavenging process from the product stream, the temperature may be below about 270° C., or, for example, from about 50° C. up to about 270° C., or, for example, from about 100° C. to about 250° C. In view of the temperature difference between the pre-reactors in oxidative dehydrogenation mode and chemisorption or oxygen scavenging mode, it may be necessary to cool the feed to the pre-reactor to be used for chemisorption or oxygen scavenging to an appropriate temperature before entering the pre-reactor in chemisorption or oxygen scavenging mode. Hence, one embodiment may have several pre-reactors to permit the pre-reactor time to cool prior to putting it into service for scavenging. Oxygen scavenging is exothermic and the reactor will heat up and, depending on the catalyst system, oxygen release could be exothermic so the heat requirements may not be to significant (e.g., near neutral).

Figure 2:
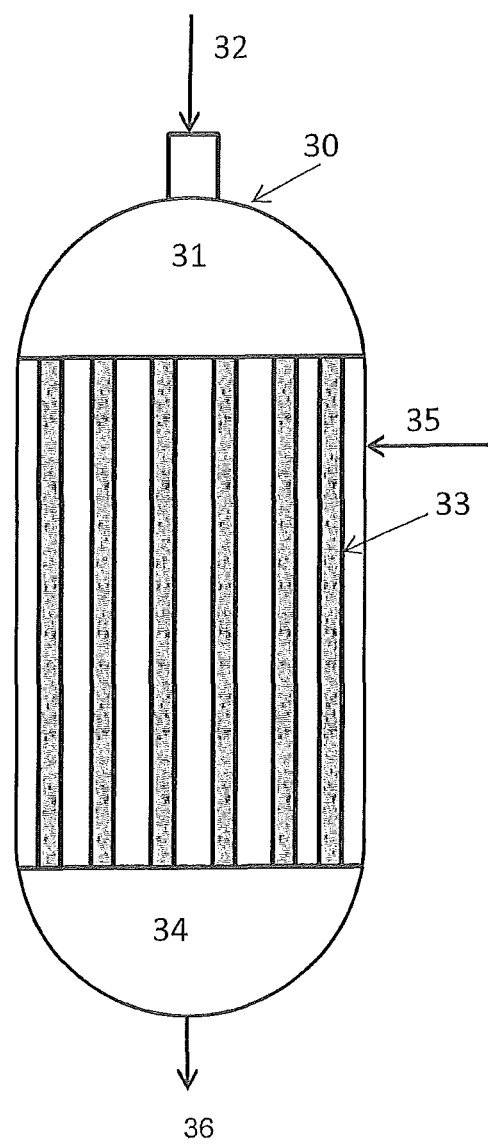
FIG. 2 is a schematic diagram of a main reactor in which the oxidative dehydrogenation takes place on the surface of ceramic tubes.

FIG. 2 shows an embodiment of a main reactor comprising a membrane (ceramic tube) oxidative dehydrogenation reactor. The reactor is generally shown as 30. The reactor comprises an inlet 31 into which a stream of ethane or an ethane containing gas 32 flows. The ethane passes through the ceramic membrane tubes 33 to a collector 34. Oxygen or an oxygen containing gas 35 is fed to the tube bundle so the oxygen is on the outside of the tubes. The ethane or ethane containing gas 32 reacts with the oxygen as it passes down the tube to form ethylene. The ethylene is collected in the collector (footer) 34 and exits the reactor at 36.

Figure 3:
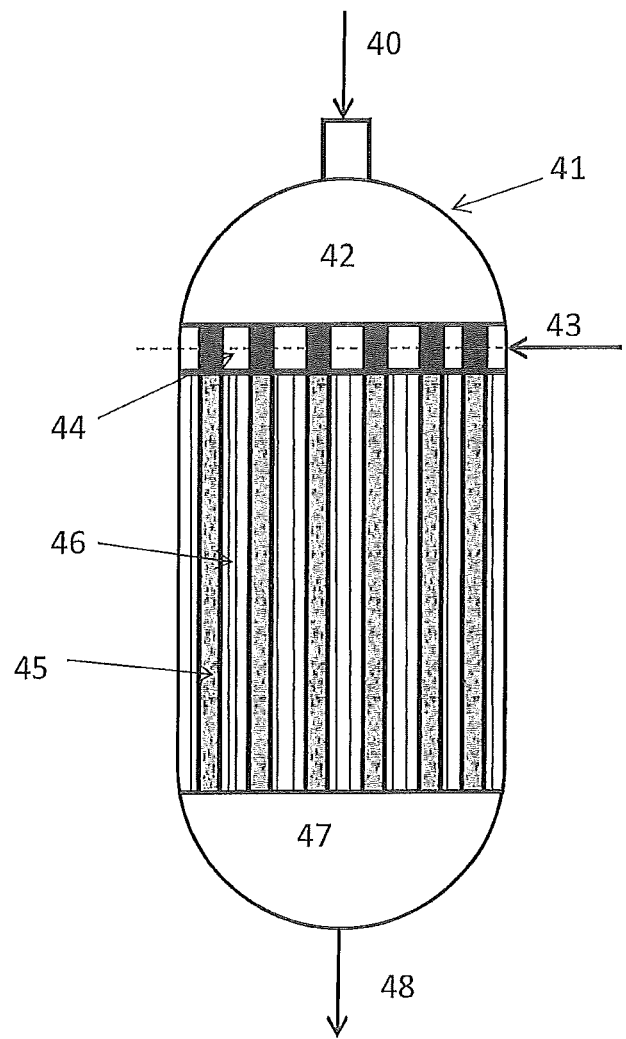
FIG. 3 is a schematic diagram of a main reactor in which the oxidative dehydrogenation takes place on the surface of ceramic tubes.
Figure 3:
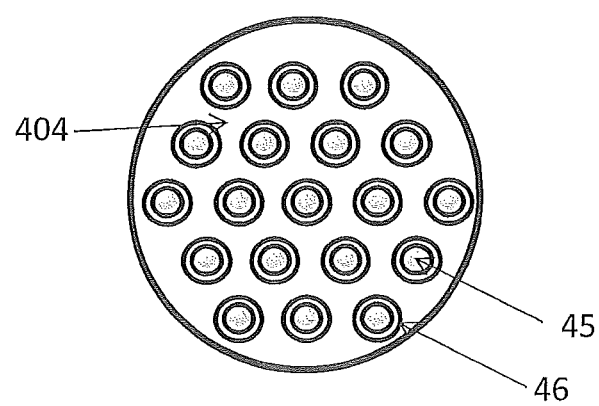

FIG. 3 shows a further embodiment of a main reactor comprising a ceramic membrane in which the ethane or ethane containing gas 40 enters the reactor generally shown as 41 through an inlet or 42. The oxygen or oxygen containing gas 43 enters a tube and shell type plate shown at 44. There are a series of ceramic membrane tubes 45 encased in a steel shell 46. The ceramic membrane tubes 45 extend up to the header 42. As a result, the ethane or ethane containing gas 40 flows down the interior of the ceramic membrane tubes and the oxygen flows down the annular space between the exterior of the ceramic membrane tube 45 and the steel shell 46. The ethane is converted to ethylene and exits the ceramic membrane tubes into collector (footer) 47 and exits at 48. One advantage of this design is if a ceramic membrane loses integrity excess oxygen only enters that tube. This is easily detected by an oxygen detector (not shown) which may be at the exit of each tube 45 or in the collector 47. Then the reactor can be safely shut down and the damaged tube may be located.

The flows of the reactants may be co-current or counter current (e.g., ethane up the outside of the tube and oxygen down the inside of the tube).

The feed to the reactor comprises two separate flows to opposite sides of a tube. In one further embodiment, one flow, for example, to the internal surface of the tube is an oxygen containing gas which is selected from oxygen, mixtures comprising from 100 to about 21 vol. % of oxygen and from 0 to about 79 vol. % of one or more inert gases. Some inert gases may be selected from nitrogen, helium and argon and mixtures thereof. The oxygen containing gas could be air.

The Reaction

The oxidative dehydrogenation in the main reactor may be conducted at temperatures from about 300° C. to about 550° C., or, for example, from about 300° C. to about 500° C., or, for example, from about 350° C. to about 450° C., at pressures from about 0.5 to about 100 psi (about 3.447 to about 689.47 kPa), or, for example, from about 15 to about 50 psi (about 103.4 to about 344.73 kPa), and the residence time of the paraffin (e.g., ethane) in the reactor is typically from about 0.002 to about 30 seconds, or, for example, from about 1 to about 10 seconds. The paraffin (e.g., ethane) feed may be of purity of about 95%, or, for example, about 98%. In one embodiment, the process has a selectivity for olefin (ethylene) of greater than about 95%, or, for example, greater than about 98%. The gas hourly space velocity (GHSV) may be from about 500 to about 30000 h$^{-1}$, or, for example, greater than about 1000 h$^{-1}$. The space-time yield of ethylene (productivity) in g/hour per kg of the catalyst may be not less than about 900, or, for example, greater than about 1500, or, for example, greater than about 3000, or, for example, greater than about 3500 at about 350 to about 400° C. Without wishing to be bound by theory, it is speculated that the productivity of the catalyst may increase with increasing temperature until the selectivity is sacrificed.

The conversion of ethane to ethylene may be not less than about 80%, or, for example, greater than about 90%, or, for example, about 95% or greater.

The oxygen feed may be pure oxygen however this is expensive. The feed may comprise about 95 vol. % of oxygen and about 5 vol. % of argon. This stream is a bi-product of nitrogen production and relatively inexpensive. Argon, being inert, should not interfere with any downstream reactions.

Oxygen Scavenging

The amount of oxygen that is entrained in the product ethylene stream may be minimized for further processing. However, there will likely be some small amount of oxygen in the product stream. It is highly desirable that the oxygen be removed from the product stream prior to further processing of the product stream. Immediately downstream of the oxidative dehydrogenation reactor may be a low temperature (below about 270° C.) pre-reactor in which the oxidative dehydrogenation catalyst has a reduced reactive oxygen content to take up residual oxygen from the product stream without oxidizing more than about 5 wt. %, or, for example, less than about 1 wt. % of the ethylene produced. The low temperature oxygen scavenging reactor operates at temperatures less than or equal to about 300° C., or, for example, from about 50° C. to about 300° C., or, for example, from about 50° C. to about 270° C., or, for example, from about 50° C. to about 270° C., or, for example, from about 50° C. to about 250° C., or, for example, from about 100° C. to about 250° C.

In some embodiments of operation, the process may balance the oxygen feed to the main reactor depending on the conversion in pre-reactor 4.

There may be several "pre-reactors" also used as scavengers to accommodate the product flow out of the main reactor. It may not be so much of an issue with the pre-reactor operating in oxidative dehydrogenation mode since any excess alkane not dehydrogenated in the pre-reactor may be converted in the main reactor(s). The key issue is the scavenging of oxygen from the product stream.

In some embodiments, at the exit of the main oxidative dehydrogenation reactor is an oxygen sensor. Additionally, there may be an oxygen sensor at the exit for the dehydrogenated product from each pre-reactor to determine the oxygen level leaving the process chain. When the oxygen level rises at the dehydrogenated product outlet of the pre-reactor (i.e., scavenger reactor) it indicates the catalyst has substantially taken up reactive oxygen (and may be returned to use as a pre-reactor). The amount of reactive oxygen uptake by the oxygen depleted catalyst in the pre-reactor operation in oxygen scavenging or chemisorption mode may be not less than about 1.5%, typically about 2% of the total oxygen in the catalyst (this will also correspond to the amount of reactive oxygen available for release from the catalyst in the pre-reactors in oxidative dehydrogenation mode).

Figure 9:
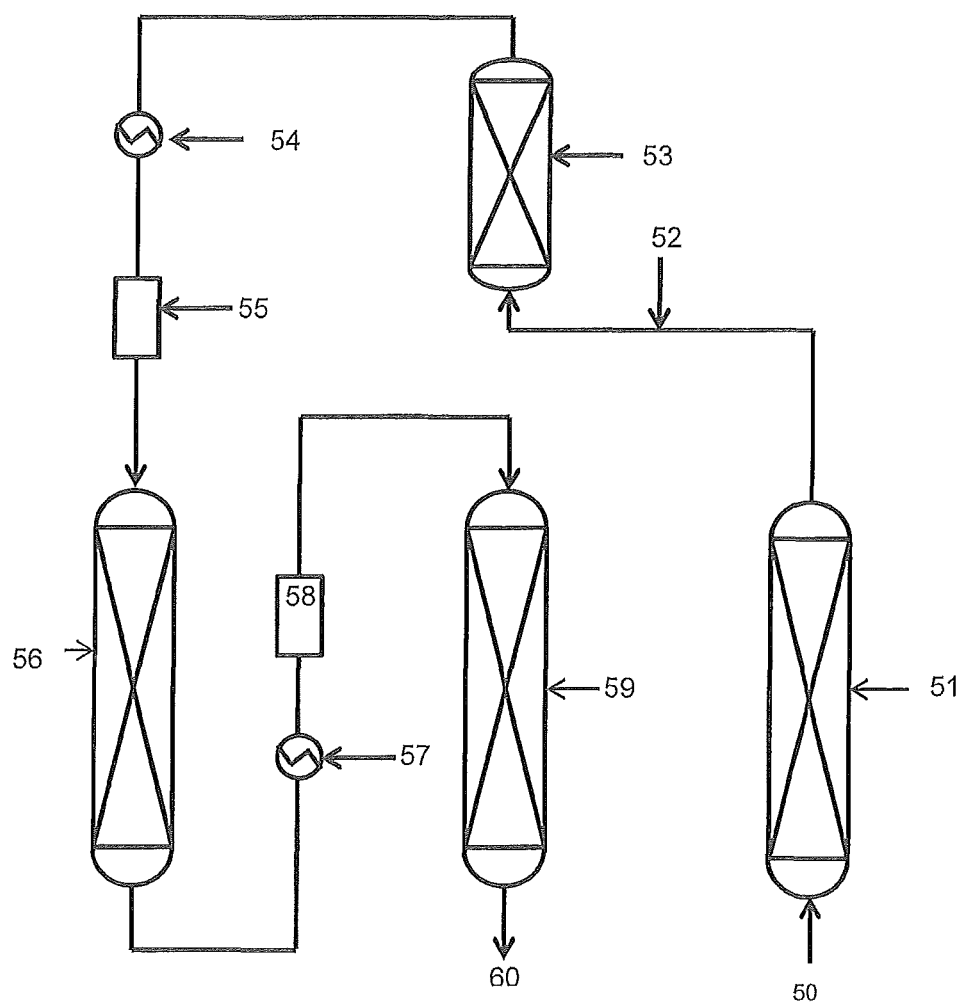
FIGS. 9, 10 and 11 illustrate how a series of three fixed bed catalysts may be used to scavenge oxygen from the product stream in an oxidative dehydrogenation reactor.
Figure 10:
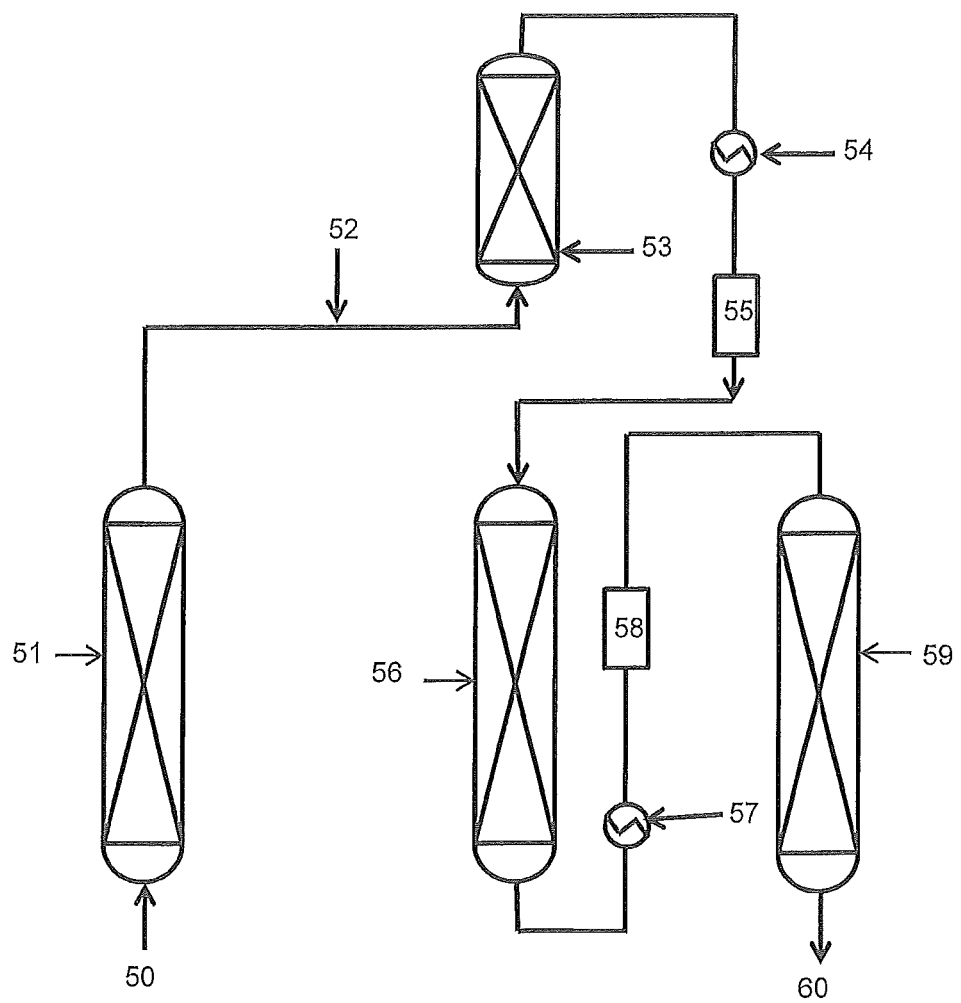
Figure 11:
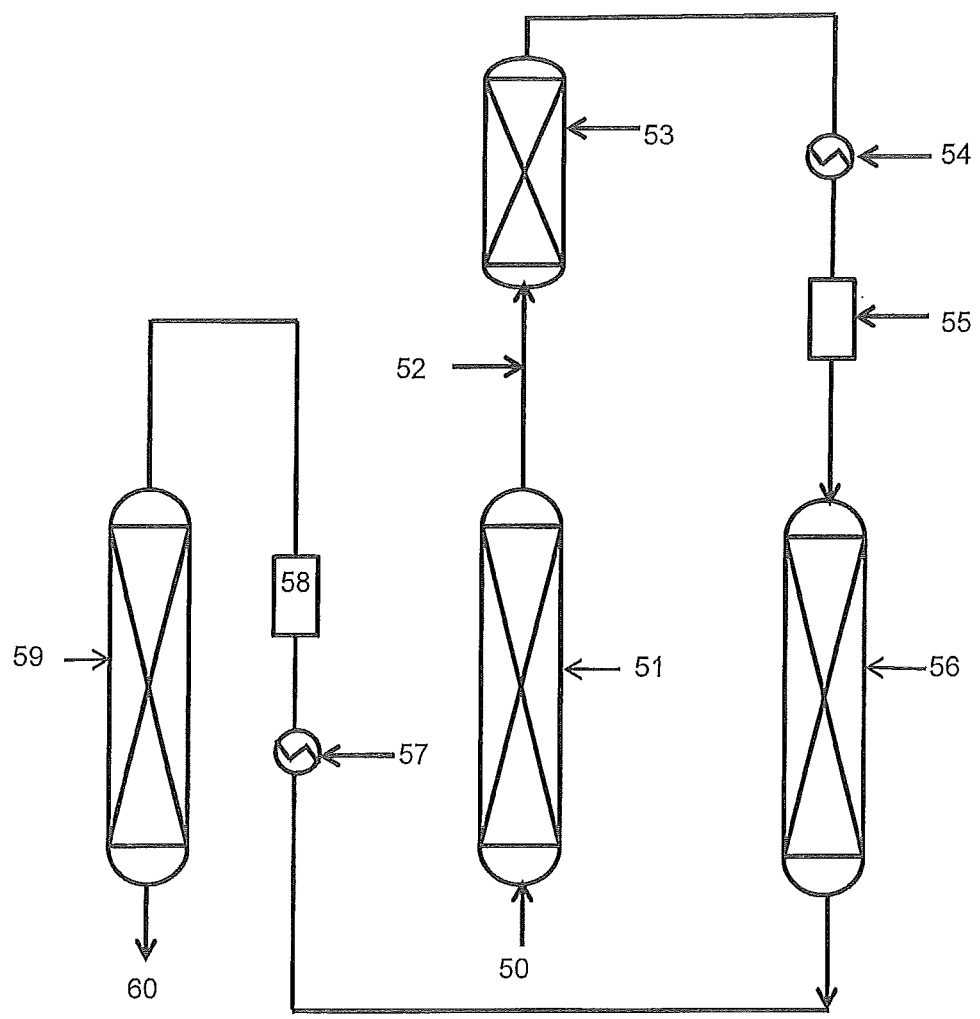

One mode for operation using three pre-reactors is illustrated schematically in FIGS. 9, 10, and 11 (in which like parts have like numbers) and the table below. In FIGS. 9, 10, and 11, the valves are not shown. The main reactor configuration is the same, however, the switching of the valves causes the pre-reactor, scavenger reactor and the guard reactor to appear to "switch" places. One pre-reactor operates as such and converts part of the feed stream to ethylene. One oxygen depleted pre-reactor acts as a primary oxygen scavenger or chemisorption reactor and a second pre-reactor (also oxygen depleted acts as a guard or secondary oxygen scavenger or chemisorption reactor).

| Process Step | Operation<br>Process streams flow sequence |
|---|---|
| Step 1<br>(FIG. 9): | Ethane (50) is routed to a pre-reactor (51) (optionally oxygen saturated). Some of the ethane is converted to ethylene and the product together with oxygen (52) is routed to the main reactor (53), where most or all ethane is converted to ethylene. The product is cooled in a condenser (54) to a temperature from 50° C. to 270° C., and optionally water is knocked out of the product stream in knock out drum (55) (adsorbed by one or more guard beds). The cooled product stream is routed to a primary oxygen depleted pre-reactor which acts as a lead oxygen scavenger reactor (56). Oxygen scavenging/chemisorption is exothermic, the product stream from the primary oxygen scavenging reactor may be cooled in a condenser (57) and routed through water knock out drum (58) to the secondary or guard oxygen scavenger reactor (59) (oxygen depleted pre-reactor) - (cooling down may not be required, since the only reason for cooling is to reduce any oxidation reaction of the final product (60) (e.g., production of CO and $CO_2$ or both), in the secondary or guard oxygen depleted pre-reactor initially there is a very low level of reactive oxygen (typically, less than 50, or, for example, less than 25, or, for example, less than 10 ppm of reactive oxygen in the feed stream) may be present; A slightly elevated temperature (2° C. to 5° C. higher) will help to remove it to very low level without converting the product to CO and $CO_2$. Oxygen sensors, not shown, are active on inlets to the lead (primary) and guard (secondary oxygen scavengers and the outlet of the guard scavenger. The operation is to go to step 2 when the oxygen content in the product stream exiting the guard reactor exceeds specified value. |
| Step 2:<br>(FIG. 10) | Changes from Step 1 (FIG. 9): The former pre-reactor (51) now becomes guard scavenger (59); former guard scavenger (59) now becomes lead scavenger (56), former lead scavenger (56) becomes pre-reactor (51). Operation is the same as described for the Step 1. |
| Step 3:<br>(FIG. 11) | Changes from Step 2 (FIG. 10): Pre-reactor (51) becomes guard scavenger reactor (59); former guard scavenger becomes lead scavenger reactor (56,) and former lead scavenger becomes the pre-reactor (51). Operation is the same as described for the Step 1. |
| Step 4:<br>(FIG. 9) | Return to Step 1. |

This mode of operation is beneficial, because the efficiency of most adsorption/chemisorption processes is limited by mass transfer front or zone (MTZ). As a result, a significant part of the oxygen scavenging material remains not saturated with oxygen, and consequentially once the scavengers is switched into the pre-reactor mode, the pre-reactor will have shorter run time compared to the fully oxygen saturated pre-reactor (on start-up). Having lead and guard scavengers permits a better take up of oxygen in the lead scavenger chemisorption reactor (pre-reactor). This option also gives the benefit of having an oxygen sensor between lead and guard scavengers and to having the option to switch the operation exactly at the point in time when the lead is fully saturated or to keep it on stream slightly longer, if there is a process upset of any nature requiring longer operation without switching. Another benefit of this option is that lead scavenger has to be significantly colder than the main reactor; it is to avoid ethylene oxidation reaction from occurring. The guard scavenger may be hotter than the lead scavenger, since most of the oxygen is removed and to remove trace oxygen higher temperature is beneficial. Oxidation of the product stream in the guard scavenger is not expected to occur to any significant extent, since only traces of oxygen are present. Because of the operation as described above, when pre-reactor (converter) switches to be a guard scavenger, it is still hot, which is very beneficial for the guard, when guard switched to be the lead, it is already cooled with ethylene product in the most efficient way, by direct contact of ethylene product with the surface of the catalyst.

The resulting product is then passed down stream for optional further separation. The separation requirements are minimized in the present reaction as the catalyst in the main reactor has a selectivity above about 95% or, for example, above about 98% and no or a minimum amount of by-products are produced in the oxygen scavenging step. The product can be sent directly to polymerization plant or other ethylene derivatives plants, (such as, ethylene glycol, acetic acid, vinyl acetate, etc.) as they can utilize ethylene of a lower purity, alternately only CO, $CO_2$ may be separated or $CO_2$ only, if needed. However, as noted above, in one embodiment, the pre-reactor is operated in chemisorption or oxygen scavenging mode at a temperature to minimize further generation of carbon dioxide, carbon monoxide or both.

EXAMPLES

The present invention will now be illustrated by the following non-limiting examples.

Figure 4:
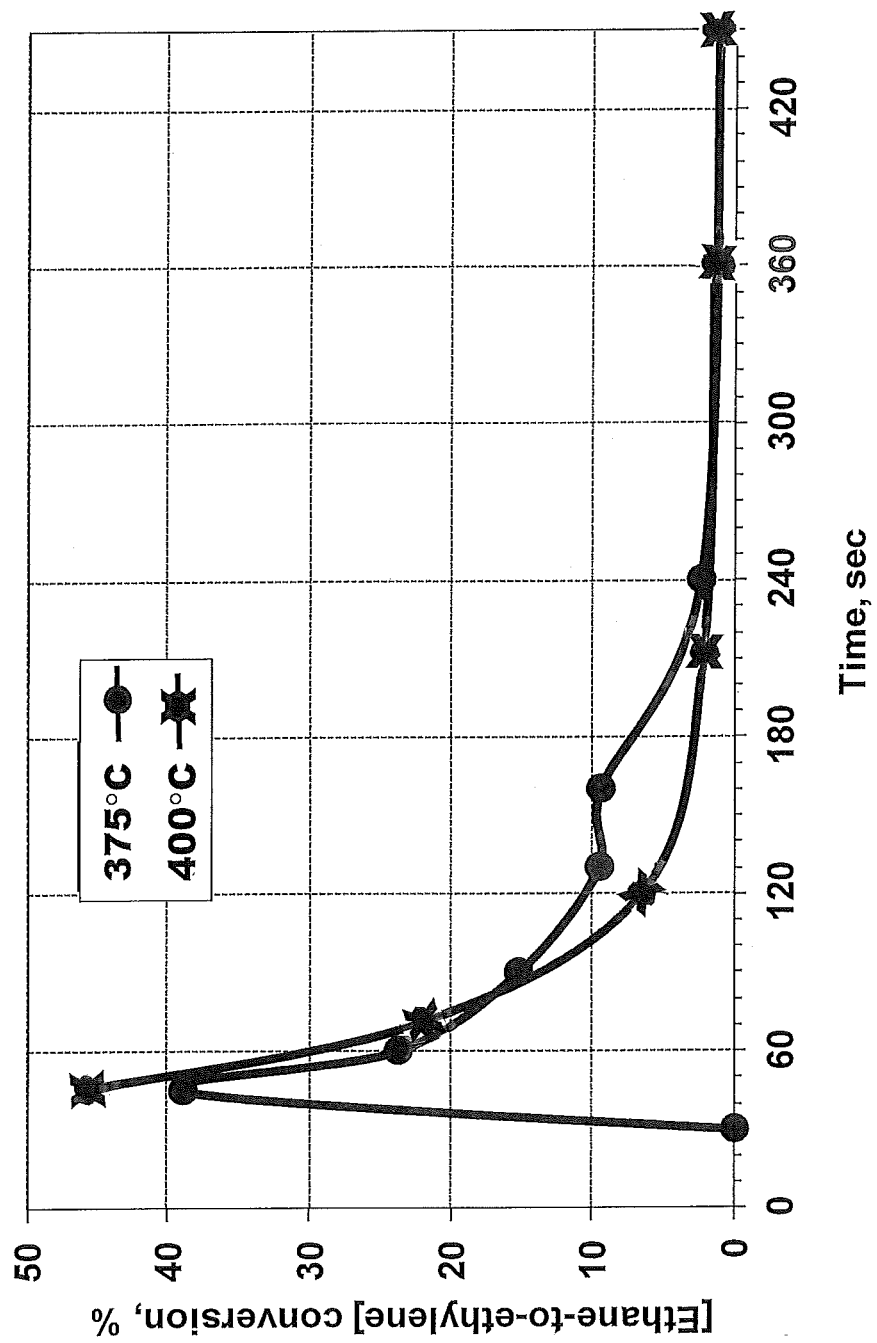
FIG. 4 shows the reaction profile (Dynamics) of ethylene formation as a function of time at 375° C. and 400° C. after the gas flow switch [air→ethane] for a $Mo_1$—$V_{0.3}$—$Nb_{0.2}$—$Te_{0.1}$—$O_X$ catalyst with 80% of $TiO_2$ as support.
Figure 5:
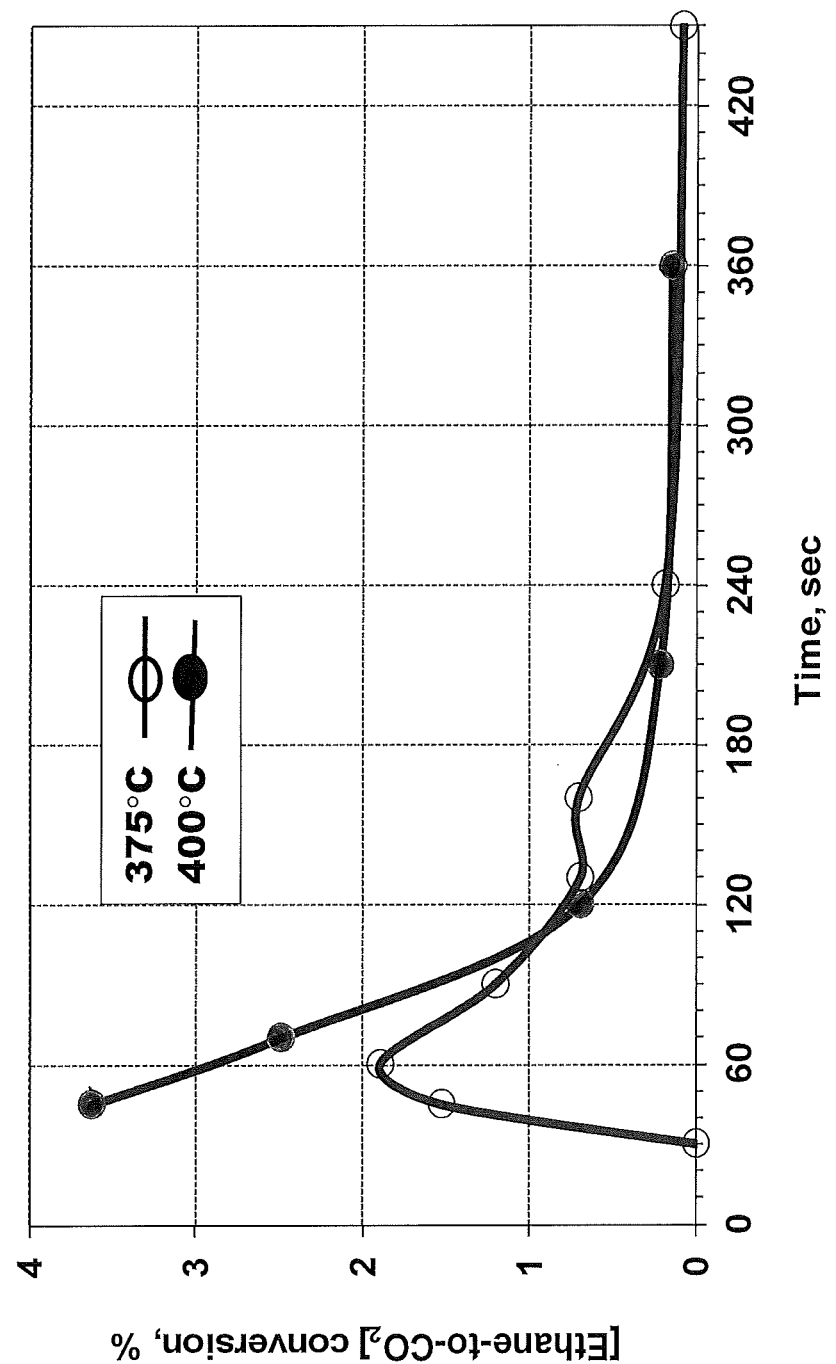
FIG. 5 shows the reaction profile (Dynamics) of $CO_2$ formation as a function of time at 375° C. and 400° C. after the gas flow switch [air→ethane]; for a $Mo_1$—$V_{0.3}$—$Nb_{0.2}$—$Te_{0.1}$—$O_X$ catalyst with 80% of $TiO_2$ as a support.
Figure 6:
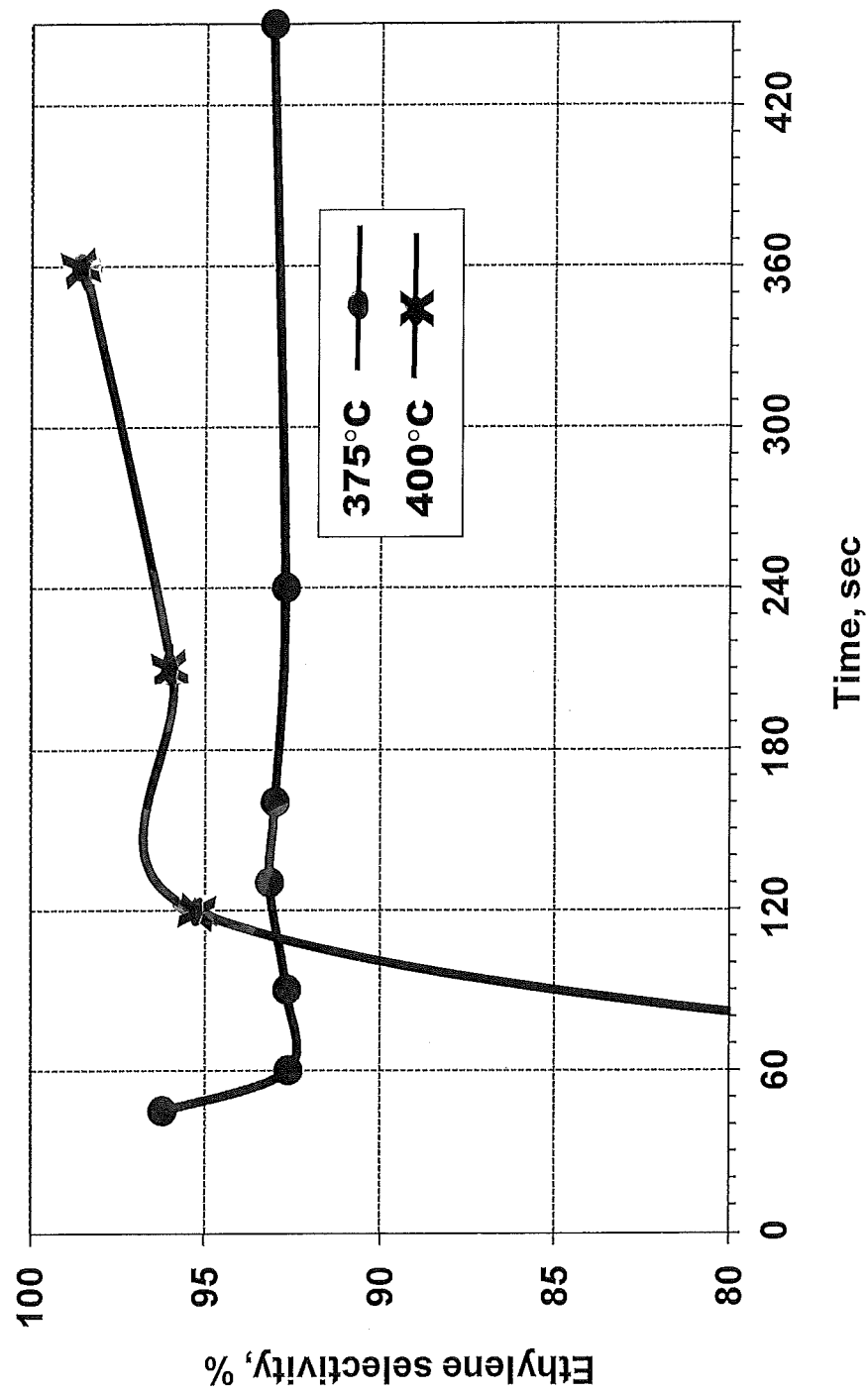
FIG. 6 shows the selectivity of ethylene formation of time at 375° C. and 400° C. after the gas flow switch [air→ethane]; for a $Mo_1$—$V_{0.3}$—$Nb_{0.2}$—$Te_{0.1}$—$O_X$ catalyst with 80% of $TiO_2$ as a support.

1. Scavenging (Post-Removal) of Residual Oxygen from the Ethylene Product Gas Mixture by the Periodical Redox Cycle Scavenging of residual oxygen from the product (outgoing gas) mixture was realized by cyclical periodical redox operation mode. In this case, a $Mo_1$—$V_{0.3}$—$Nb_{0.2}$—$Te_{0.1}$—$O_X$ catalyst or other Oxygen Storage Material (OSM) can be used in the two-step process. Step 1 provides the reduction of the OSM layer by pure ethane at temperatures ~400° C., and Step 2 supports absorptive removal of the residual $O_2$ from the outgoing product mixture by the pre-reduced layer working as an OSM at a reduced temperature. It was shown that the $Mo_1$—$V_{0.3}$—$Nb_{0.2}$—$Te_{0.1}$—$O_X$ catalyst itself served as a rather effective OSM at 300-400° C.

a) Step 1: Reduction of the $Mo_1$—$V_{0.3}$—$Nb_{0.2}$—$Te_{0.1}$—$O_x$ Catalyst Layer by Pure Ethane Measurements were done using a fresh sample [20% Mo—V—Te—Nb-$O_X$+80% $TiO_2$ (support)] prepared by mechanical methods (grinding and compaction/extrusion). In this testing, the sample (2.0 cm$^3$; 2.97 g, particle size 0.2 to 0.4 mm) was placed into a quartz reactor and heated to a specified temperature (375° and 400° C.) in an air flow, for 15 min, then the gas flow (900 cm$^3$/h) was switched to pure ethane, and a probe of the outgoing mixture was taken for analysis after a given time. After re-oxidation of the sample by air for 15 min., measurements were repeated several times with varying the time interval, and resulting response curves of products were obtained (up to 7.5 min). FIGS. 4, 5, and 6 demonstrate the time dependence of ethylene and $CO_2$ formation rates as well as the selectivity of ethylene formation upon the catalyst reduction by pure ethane at two different temperatures. The CO formation curves are quite similar to those observed for $CO_2$ (FIG. 5).

FIG. 4 shows the reaction profile (Dynamics) of ethylene formation as a function of time at 375° C. and 400° C. after the gas flow switch [air→ethane] for a $Mo_1$—$V_{0.3}$—$Nb_{0.2}$—$Te_{0.1}$—$O_X$ catalyst with 80% of $TiO_2$ as support.

FIG. 5 Shows the reaction profile (Dynamics) of $CO_2$ formation as a function of time at 375° C. and 400° C. after the gas flow switch [air→ethane]; for a $Mo_1$—$V_{0.3}$—$Nb_{0.2}$—$Te_{0.1}$—$O_X$ catalyst with 80% of $TiO_2$ as a support.

FIG. 6 shows the selectivity of ethylene formation of time at 375° C. and 400° C. after the gas flow switch [air→ethane]; for a $Mo_1$—$V_{0.3}$—$Nb_{0.2}$—$Te_{0.1}$—$O_X$ catalyst with 80% of $TiO_2$ as a support.

Thus, the step of the catalyst reduction by pure ethane at 380 to 400° C. is accompanied by the formation of ethylene with a selectivity >92% (FIG. 6).

The results obtained permit one to calculate the total amount of the "reactive" lattice oxygen in the catalyst working as an OSM. Integration of the response curves (FIGS. 4 and 5) being produced at a constant ethane flow rate of 37.5 mmol/h permits one to evaluate the overall amount of oxygen reacted during the catalyst reduction step. Taking into account that 1 g of the mixed oxide ($Mo_1$—$V_{0.3}$—$Nb_{0.2}$—$Te_{0.1}$—$O_X$ contains ~333 mg of oxygen, we can conclude that ~1.9% from this amount (~6.3 mg/g) can be removed from the active phase by reduction. Thus, the oxygen storage (absorption) capacity upon the subsequent re-oxidation step cannot exceed this number.

(b) Step 2: Absorption of the Residual $O_2$ from the Outgoing Mixture by the Pre-Reduced Layer Working as an Oxygen-Storage Material at a Reduced Temperature In this testing, the sample of catalyst after reduction by pure ethane at 400° C. for 15 min. was cooled to a given temperature (270° C.) in the ethane flow, then model product gas flow ([49.5% vol. $C_2H_6$+46.7% vol. $C_2H_4$+3.8% vol. $O_2$+$CO_2$-traces]; 720 cm$^3$/h) was switched on, and the probe of the outgoing mixture was taken for analysis after a given time. After subsequent reduction of the sample by ethane (15 min., 400° C.), measurements were repeated several times with varying the time interval, and the resulting response curves of products were produced (up to 5 min.). The same testing was repeated at 400° C. for comparison. FIGS. 1 and 8 demonstrate the time dependence of the total $O_2$ removal, as well as the variation of the CO and $CO_2$ concentrations in the product flow from the scavenging reaction flow at 270° C. and 400° C.

Figure 7:
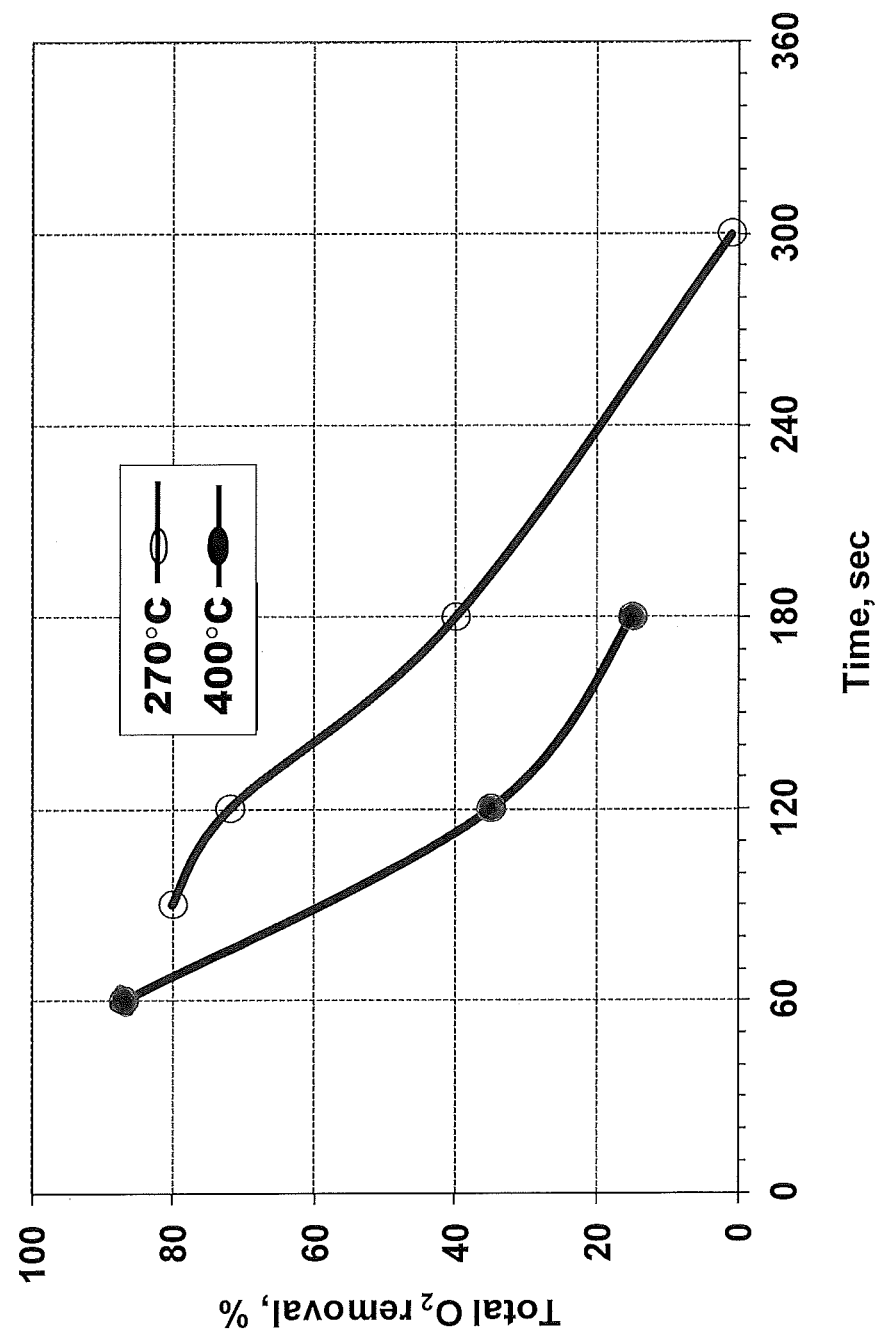
FIG. 7 shows the reaction profile (Dynamics) of $O_2$ removal from the model gas mixture by the pre-reduced catalyst of $Mo_1$—$V_{0.3}$—$Nb_{0.2}$—$Te_{0.1}$—$O_X$ supported on 80% of $TiO_2$ at 270° C. and 400° C.

FIG. 7 shows the reaction profile (Dynamics) of $O_2$ removal from the model gas mixture by the pre-reduced catalyst of ($Mo_1$—$V_{0.3}$—$Nb_{0.2}$—$Te_{0.1}$—$O_X$ supported on 80% of $TiO_2$ at 270° C. and 400° C.

Figure 8A:
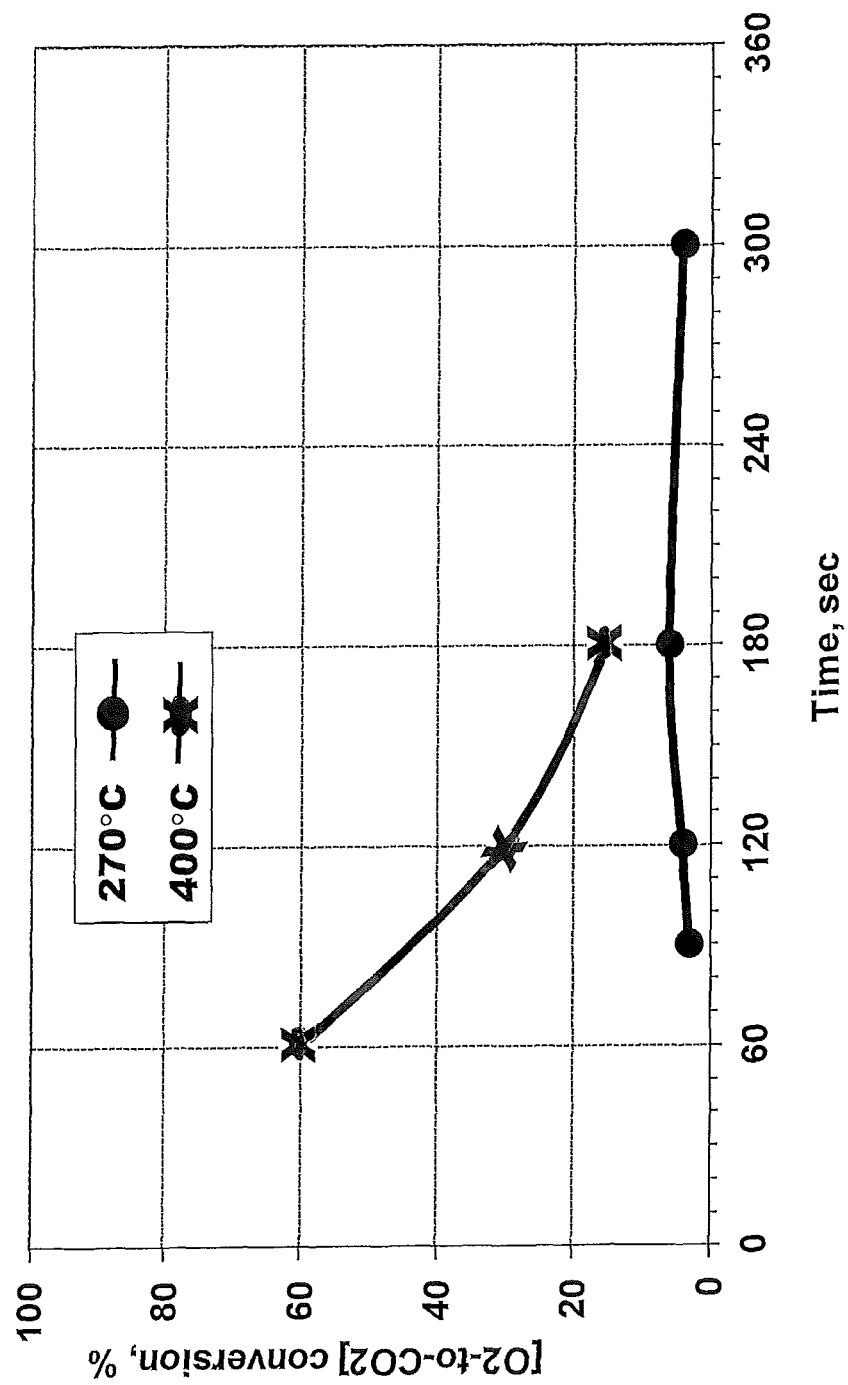
FIG. 8a shows the reaction profile (Dynamics) of $CO_2$ and FIG. 8b shows the reaction profile (Dynamics of CO formation after feeding the model gas mixture by the pre-reduced catalyst of $Mo_1$—$V_{0.3}$—$Nb_{0.2}$—$Te_{0.1}$—$O_X$ supported on 80% of $TiO_2$ at 270° C. and 400° C.
Figure 8B:
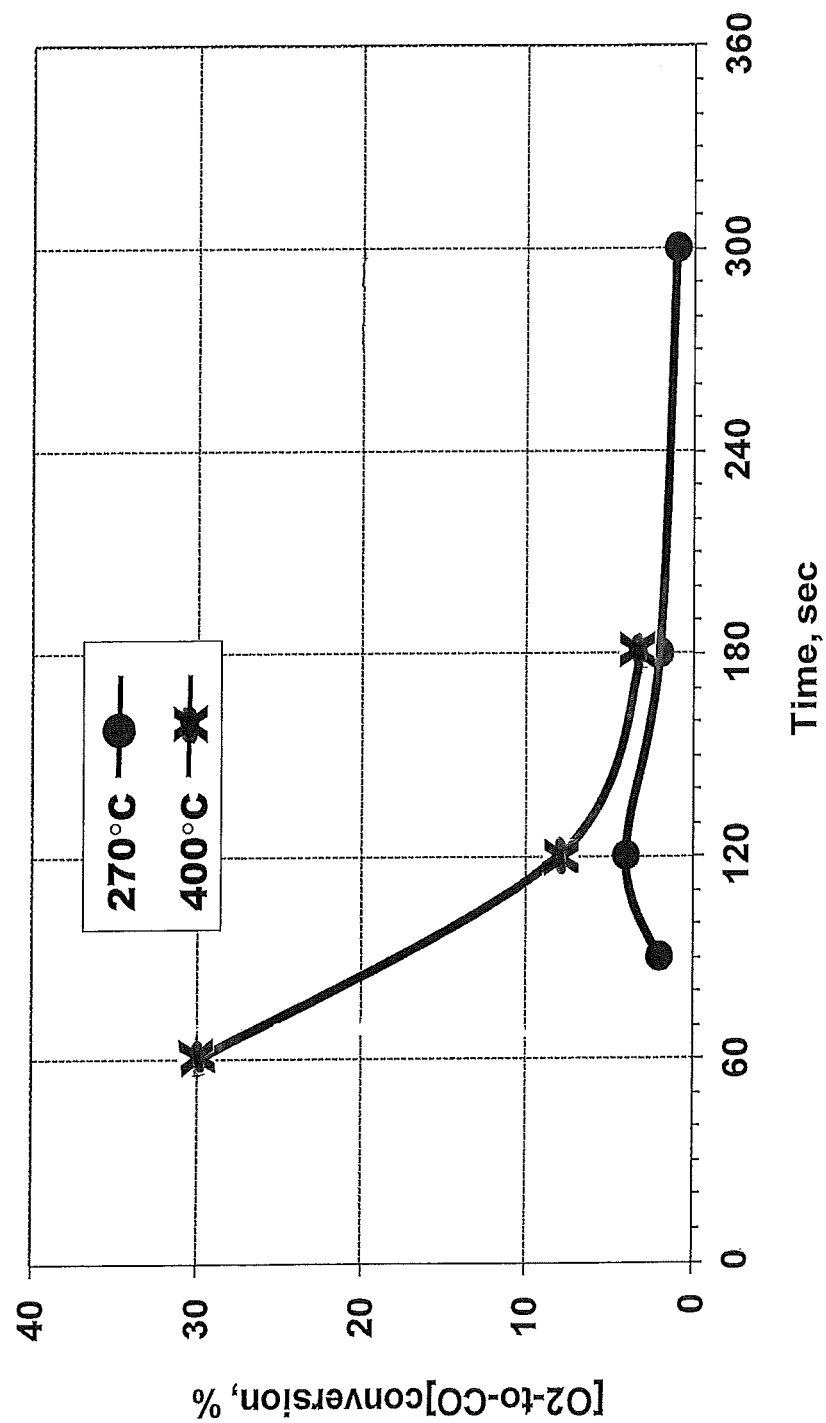

FIGS. 8a and b show the reaction profile (Dynamics) of $CO_2$(a) and CO(b) formation after feeding the model gas mixture by the pre-reduced catalyst of ($Mo_1$—$V_{0.3}$—$Nb_{0.2}$—$Te_{0.1}$—$O_X$ supported on 80% of $TiO_2$ at 270° C. and 400° C.

As one can see, a very considerable formation of both CO and $CO_2$ takes place at 400° C., i.e., not absorption of oxygen but rather catalytic oxidation proceeds at a high temperature even on the pre-reduced catalyst. The situation changes after the temperature reduction: at 270° C. the absorptive $O_2$ removal becomes the main process, with a minor contribution of both CO and $CO_2$ formation.

What is claimed is:
1. A process for the catalytic oxidative dehydrogenation of one or more $C_{2-4}$ alkanes comprising at least three pre-reactors and one or more downstream main oxidative dehydrogenation reactors comprising:
  i) passing a feed stream comprising said one or more $C_{2-4}$ alkanes through a first pre-reactor containing a dehydration catalyst that is saturated with reactive oxygen;
  ii) reacting the feed stream with the dehydration catalyst that is saturated with reactive oxygen at a temperature from about 300° C. to about 500° C. and a pressure from about 0.5 to about 100 psig to produce a partially dehydrogenated stream comprising unreacted $C_{2-4}$ alkanes;
  iii) passing the partially dehydrogenated stream together with additional oxygen feed to one or more downstream main oxidative dehydrogenation reactors;
  iv) oxidatively dehydrogenating the partially dehydrogenated stream at a temperature from about 300° C. to about 500° C. and a pressure from about 0.5 to about 100 psig to produce a product stream;
  v) removing the product stream from said one or more downstream main oxidative dehydrogenation reactors comprising corresponding $C_{2-4}$ alkenes, unreacted $C_{2-4}$ alkanes, unreacted oxygen and water vapor;
  vi) passing the product stream through a series of two or more pre-reactor comprising a lead and a guard dehydrogenation reactor having secondary dehydrogenation catalyst that are depleted of reactive oxygen the lead dehydrogenation reactor having a secondary dehydro- genation catalyst that is less depleted of reactive oxygen than the dehydrogenation catalyst in the guard dehydrogenation reactor;
vii) reacting the product stream with the dehydrogenation catalyst of the lead dehydrogenation reactor depleted of reactive oxygen at a temperature from about 50° C. to about 270° C. and a pressure from about 0.5 to about 100 psig to complex the oxygen depleting oxygen from the product stream and regenerating oxidative dehydrogenation catalyst by increasing the saturation with reactive oxygen; and
viii) reacting the product stream from the lead dehydrogenation reactor with the reactive oxygen depleted catalyst of the guard oxygen dehydrogenation reactor at a temperature from about 50° C. to about 270° C. and a pressure from about 0.5 to about 100 psig to complex the oxygen depleting oxygen from the product stream and partially regenerating oxidative dehydrogenation catalyst by increasing the saturation with reactive oxygen; and
ix) recovering a product stream depleted of oxygen;
recovering a product stream depleted of oxygen;
x) continuing step (i) to (ix) until either:
  a) the pre-reactor comprising the first dehydrogenation catalyst and through which the feed stream is being passed is depleted of reactive oxygen or is more depleted or reactive oxygen than another pre-reactor; or
  b) the pre-reactor comprising the second oxidative dehydrogenation catalyst through which the product stream is being passed is substantially saturated with reactive oxygen;
xi) when condition (a) is achieved the feed stream is diverted from the first pre-reactor to lead dehydrogenation reactor that is more saturated with reactive oxygen the product stream from the main dehydrogenation reactors is diverted to the guard dehydrogenation reactor and the product stream from the guard dehydrogenation reactor is diverted to the primary dehydrogenation reactor in which the dehydrogenation catalyst is depleted of reactive oxygen and the process continues from step (i) on.

2. The process according to claim 1, wherein the oxidative dehydrogenation catalyst in any reactor is independently selected from:
  i) catalysts of the formula

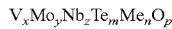

wherein Me is a metal selected from Ta, Ti, W, Hf, Zr, Sb and mixtures thereof; and
  x is from about 0.1 to about 3 provided that when Me is absent x is greater than 0.5;
  y is from about 0.5 to about 1.5;
  z is from about 0.001 to about 3;
  m is from about 0.001 to about 5;
  n is from 0 to about 2; and
  p is a number to satisfy the valence state of the mixed oxide catalyst; and
  ii) catalysts of the formula

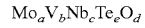

wherein:
  a is from about 0.75 to about 1.25;
  b is from about 0.1 to about 0.5;
  c is from about 0.1 to about 0.5;
  e is from about 0.1 to about 0.3; and
  d is a number to satisfy the valence state of the mixed oxide catalyst.

3. The process according to claim 2, wherein said one or more downstream main oxidative dehydrogenation reactors are operated at a gas hourly space velocity (GHSV) from about 500 to about 30000 $h^{-1}$.

4. The process according to claim 3, wherein the catalyst in the main reactor is supported on an inert metal oxide support having a surface area of less than about 5 $m^2/g$.

5. The process according to claim 4, wherein the pre-reactors are fixed bed reactors and the oxidative dehydrogenation catalyst is supported on an inert metal oxide support having a surface area of not less than about 100 $m^2/g$.

6. The process according to claim 5, wherein said one or more downstream main oxidative dehydrogenation reactors are selected from fixed bed reactors, fluidized or ebullated bed reactors, and ceramic membrane reactors.

7. The process according to claim 6, having a selectivity for said one or more $C_{2-4}$ alkenes of greater than about 85%.

8. The process according to claim 7, wherein said one or more $C_{2-4}$ alkanes is ethane.

9. The process according to claim 8, wherein the catalyst in said pre-reactors is of formula (ii) and wherein:
  a is from about 0.90 to about 1.10;
  b is from about 0.25 to about 0.3;
  c is from about 0.1 to about 0.3;
  e is from about 0.1 to about 0.2; and
  d is a number to satisfy the valence state of the mixed oxide catalyst.

10. The process according to claim 1, wherein in step (vi) the product stream from said downstream main oxidative dehydrogenation reactors is passed sequentially through two or more pre-reactors in which the first of these sequential pre-reactors has a higher amount of reactive oxygen in the oxidative dehydrogenation catalyst than in the subsequent pre-reactors.

11. The process according to claim 1, further comprising a third pre-reactor comprising an oxidative dehydrogenation catalyst that can accept the feed stream when enriched with oxygen or accept the product stream when substantially depleted of oxygen.

* * * * *